(12) United States Patent
Kampouris et al.

(10) Patent No.: US 8,541,239 B2
(45) Date of Patent: Sep. 24, 2013

(54) ASSAY METHOD FOR DETECTING PRIMARY AMINES

(75) Inventors: Dimitrios Konstantinos Kampouris, Athens (GR); Patrick Robinson Huddleston, Nottingham (GB); Craig Edward Banks, Sale (GB)

(73) Assignee: Oxtox Limited, Nottingham (GB)

( * ) Notice: Subject to any disclaimer, the term of this patent is extended or adjusted under 35 U.S.C. 154(b) by 98 days.

(21) Appl. No.: 13/125,286

(22) PCT Filed: Oct. 15, 2009

(86) PCT No.: PCT/GB2009/002467
§ 371 (c)(1),
(2), (4) Date: Jul. 11, 2011

(87) PCT Pub. No.: WO2010/046624
PCT Pub. Date: Apr. 29, 2010

(65) Prior Publication Data
US 2011/0312100 A1 Dec. 22, 2011

(30) Foreign Application Priority Data
Oct. 22, 2008 (GB) .................................. 0819405.2

(51) Int. Cl.
*G01N 33/50* (2006.01)
*G01N 33/00* (2006.01)

(52) U.S. Cl.
USPC ............... 436/96; 436/91; 422/430; 422/500; 422/50; 422/554; 422/547

(58) Field of Classification Search
USPC ............... 436/96, 91; 422/430, 50, 554, 547
See application file for complete search history.

(56) References Cited

U.S. PATENT DOCUMENTS

| 4,203,967 A | 5/1980 | Gallo-Torres |
| 4,276,049 A | 6/1981 | Gillessen et al. |
| 4,837,166 A | 6/1989 | De Montigny et al. |
| 6,265,220 B1 | 7/2001 | Ullman |

FOREIGN PATENT DOCUMENTS

| JP | 4081665 A | 3/1992 |
| WO | 2007028906 A2 | 3/2007 |

OTHER PUBLICATIONS

Koichi et al, PAJ of JP 04-081665, Method for Analyzing Bioamino Acid, p. 1, 1992, obtained on Dec. 31, 2012.*
Pastor-Navarro M D et al, "Automated determination of amphetamine enantiomers using a two-dimensional column-switching chromatorgraphic system for derivatization and separation", Analyst, vol. 123, No. 2, 1998, pp. 319-324, and Figure b.
Leroy P et al, "electrochemical detection of sympatomimetic drugs, following pre-column o-phthalaldehyde derivatization and reversed-phase high-performance liquid chromatography", Journal of Chromatography, vol. 282, 1983, pp. 561-568.
Database WPI Week 199217, Thompson Scientific, London, GB, AN 1992-138506 XP002564751 & JP 04 081665 A, Shimadzu Corp. Mar. 16, 1992.

(Continued)

*Primary Examiner* — Christine T Mui
(74) *Attorney, Agent, or Firm* — IPHorgan Ltd.

(57) ABSTRACT

The invention provides an assay method for the detection of a primary amine analyze in an aqueous body fluid, which method comprises contacting a sample of said body fluid at a pH below 9.5 with a thiol and an unsaturated cis-dialdehyde and testing for the presence of a pyrrole reaction product.

14 Claims, 3 Drawing Sheets

(56) References Cited

OTHER PUBLICATIONS

Figure 1:
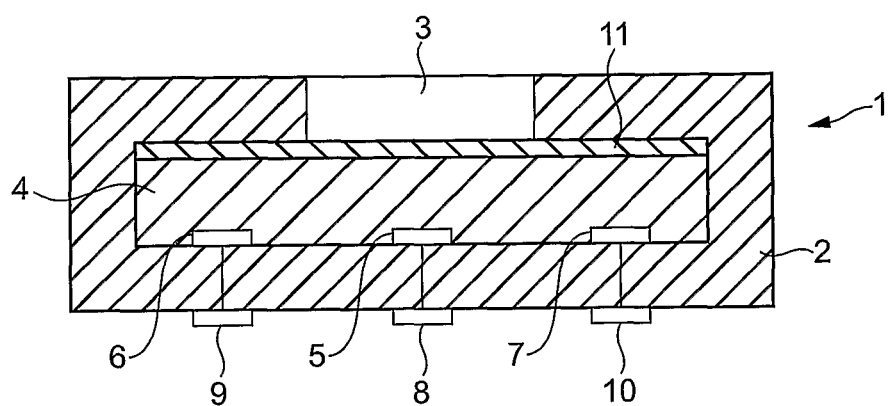

Herraez-Hernandez R et al, "Enantiomeric separation of amphetamine and related compounds by liquid chromatography using precolumn derivatization with o-phthaldialdehyde" Chromatographia, vol. 56, No. 9-10, 2002, pp. 559-565, p. 563, left hand column, paragraph 3.

Herraez-Hernandez R et al, "Derivatization techniques for automated chromatographic analysis of amphetamine using o-phthaldialdehyde: A comparative study", Chromatographia, vol. 52, No. 3-4, 2000, pp. 169-174, p. 171, paragraph 1.

European Patent Office, "International Search Report and Written Opinion", PCT/GB2009/002467, Feb. 8, 2010.

* cited by examiner

ASSAY METHOD FOR DETECTING PRIMARY AMINES

CROSS-REFERENCE TO RELATED APPLICATIONS

This application is a national stage application of PCT Application Number PCT/GB2009/002467, filed Oct. 15, 2009, claiming priority from Patent Application No. GB 0819405.2, filed Oct. 22, 2008.

This invention relates to an assay method for detecting primary amines, in particular primary amphetamines, in body fluid samples, and to apparatus for use in such a method.

Primary amphetamines, that is amphetamines with a primary amine group, such as for example 3,4-methylenedioxy-amphetamine and d- and l-amphetamine, are frequently misused as recreational drugs despite their undesirable side effects such as confusion, paranoia, depression, nausea, blurred vision and tremors. Driving while under the influence of amphetamines is thus clearly undesirable and there is a continuing need for simple, non-invasive and inexpensive techniques for determining whether an individual has recently consumed amphetamines, e.g. in roadside screening of suspected drivers or in testing of athletes.

In WO2008/003999, the contents whereof are hereby incorporated by reference, Isis Innovation described an assay for amines such as amphetamines that could be performed by electrochemical detection of the depletion of a test reagent having two redox states, one of which was capable of binding to the amine analyte. That assay method however would not discriminate between primary amines and secondary amines and it will be appreciated that for any assay used for screening it is important to minimise false positive results.

We have now found that primary amine analytes in body fluid samples may be detected by contacting the body fluid with an unsaturated cis-dialdehyde and a thiol and determining whether or not a pyrrole is produced by a ring closure reaction which traps the primary amine. Since secondary amines do not result in pyrrole formation, the incidence of false positive results is reduced. Moreover, by performing the reaction at a pH below 9.5, and particularly no higher than 8.0, amino acids and proteins which may be present in the sample do not cause pyrrole formation and so do not generate false positive results. Since the selection of the dialdehyde and thiol can result in the pyrrole that is formed by primary amine capture being fluorescent, the pyrroles produced can be particularly easy to detect.

Thus viewed from one aspect the invention provides an assay method for the detection of a primary amine analyte in an aqueous body fluid, which method comprises contacting a sample of said body fluid at a pH below 9.5, preferably at or below 8.0, with a thiol and an unsaturated cis-dialdehyde and testing for the presence of a pyrrole reaction product.

By unsaturated cis-dialdehyde is meant a compound having aldehyde (CHO) groups attached to two adjacent atoms of the compound's backbone, where the CHO groups lie on the same side of the bond between those adjacent atoms and where that bond is unsaturated. Thus, the aldehyde groups may for example be attached to a linear, branched or cyclic backbone. While virtually any such dialdehyde can be used, it is preferred that the aldehyde groups be attached in positions ortho to each other to a cyclic group, particularly an aromatic group. The use of o-phthalaldehyde and substituted derivatives thereof is especially preferred.

The thiol used may be any organic thiol, for example an alkyl thiol, particularly a $C_{1-6}$ alkyl thiol, and may carry other functional groups. The use of 2-mercapto-ethanol is especially preferred as, with primary amines and o-phthalaldehyde it produces fluorescent pyrroles (more particularly isoindoles).

By appropriate selection of specific thiols and dialdehydes, detection of the pyrrole reaction product with the particular primary amine analyte of interest may be facilitated and the incidence of false positive test results reduced. Thus for example such selection may yield pyrroles detectable at particular wavelengths by radiation absorption, scattering or emission or at particular applied voltages in electrochemical detection techniques such as cyclic voltammetry. Where cross-reactions with other compounds which may be present in the body fluid sample might reduce the accuracy of the assay method, selection of alternative dialdehydes and/or thiols can avoid this problem.

Detection of the pyrrole may be by any convenient method. Electrochemical detection and detection by absorption, emission or scattering of light are particularly preferred as they are readily effected outside the laboratory, e.g. at the roadside. Detection may involve the use of a detector apparatus or, especially where the pyrrole is fluorescent, simply the eyes of the operator.

Electrochemical detection may be effected by exposing the treated sample to an applied voltage, preferably a cycled voltage, and determining the resultant current. The unreacted reagents will either not undergo a detectable redox reaction (as is the case for o-phthalaldehyde and 2-mercapto-ethanol) or will undergo such a reaction but at a different applied voltage to that at which the pyrrole undergoes a redox reaction. Where cross-reactions might occur, they may be avoided by substitution of the backbone of the dialdehyde with electron donating or withdrawing groups. Where electrochemical detection is used, it is particularly preferred to have the dialdehyde bound to, coated on, or impregnated within the working electrode.

The electrochemical detection techniques described in WO2008/003999 and WO2006/134386, particularly cyclic voltammetry, may conveniently be used.

Before pyrrole detection is effected, the sample is preferably incubated with the dialdehyde and the thiol for a preset period, for example 1 to 20 minutes, preferably 2 to 10 minutes, e.g. 3-5 minutes.

The pH of the sample may conveniently be maintained below the specified limit by addition of an acid or, more preferably, a buffer. The sample is preferably maintained at a pH in the range 5 to 8, particularly 6 to 8, especially 6.5 to 7.5.

The body fluid that is tested may be any body fluid, e.g. blood, mucus, urine or, most preferably, saliva, and the sample may if desired be pre-treated to add or remove components, e.g. cells, water, buffer, etc.

If desired, the assay method of the invention may be combined with a further assay, e.g. as described in WO2008/003999, which detects both primary and secondary amines, in particular methamphetamines such as "ecstasy". In this way, a positive reaction on the less discriminating assay and a negative reaction on the assay according to the invention would be indicative of secondary amine use, while a double positive reaction would be indicative of primary amine use (or the use of both primary and secondary amines). Using 1,2- or 1,4-quinones, as in WO2008/003999, both assays could be run simultaneously with electrochemical detection.

As mentioned above, the assay method of the invention is especially suited for use out of the laboratory. Accordingly, it is preferred that the operator be provided with a test kit, preferably one comprising dialdehyde and thiol containing cartridges which can be loaded with the sample and, if necessary a separate detector which can be used to read the loaded cartridges.

Thus viewed from a further aspect the invention provides a kit comprising an unsaturated cis-dialdehyde, a thiol, optionally a buffer, optionally an absorbent pad, optionally a pyrrole detector, and optionally instructions for performance of a method according to the invention.

Viewed from a still further aspect the invention provides an assay cartridge comprising a casing having an aperture for placement of a body fluid sample and containing a water-absorbent pad, a thiol, and an unsaturated cis-dialdehyde.

The cartridge preferably is provided packed in a water-tight container, e.g. a foil sachet, to prevent degradation before use. The cartridge is conveniently in the form of a stick, plate or tablet to allow easy insertion into a pyrrole detector or to allow ready illumination with a fluorescence inducing radiation if to be read by eye.

If pyrrole detection is to be by electrochemical means, the cartridge preferably also is provided with electrodes positioned to be in electrical contact with the pad when the latter is wet and with electrical contacts which, when the cartridge is placed in a detector, will allow a voltage to be applied in the wet pad from an electrical source in the detector. While no electrodes are strictly necessary within the cartridge as electrodes in the detector may be brought into contact with the wet pad when it is inserted within the detector, it is preferred that three electrodes be present, a working electrode, a counter-electrode and a reference electrode. These may be of any conventional material; however it is preferred that the working electrode be a carbon-based electrode. In the case where electrodes are present, the dialdehyde is preferably bound to, coated upon or impregnated into the working electrode. The thiol and an optional but preferred buffer may be positioned similarly or impregnated into the pad. When detection is by radiation emission, scattering or absorbance, the thiol and the dialdehyde are preferably impregnated into or coated onto the pad.

Where pyrrole detection is to be by radiation emission, scattering or absorbance, the cartridge preferably has an aperture or radiation-translucent window allowing radiation from the pad to be detected.

In order to reduce the likelihood of cross reactions with large biomolecules present in the sample, e.g. proteins, the cartridge is preferably provided with a semi-permeable membrane covering the surface of the pad to which the sample is applied and which is permeable to the primary amine analyte of interest. The membrane may be for example of cellulose acetate. Where radiation from the pad is to be detected, then either this membrane should be translucent to the relevant wavelengths or a separate window or aperture to the pad should be provided.

Pyrrole detection may be quantitative, semi-quantitative or qualitative, for example giving a value for the analyte concentration in the body fluid or an indication as to whether the analyte concentration is above or below one or more pre-set values. Desirably, the pyrrole detector will have a display to allow the operator to see the detected "value". Also desirably, the detector will record the detected value and the identity of the cartridge. Cartridge identity can be determined by coding the surface of the cartridge in a manner readable by the detector, e.g. using a bar code or the like.

The assay method of the invention will generally involve calibration of the selected reagents and detection techniques using standards, i.e. aqueous samples containing known concentrations of the analyte(s) of interest. The calibration values may also be encoded into the cartridge identification so that there is no batch-to-batch variation when cartridges of different batches are read with the same detector.

The detector will preferably also include a timer so that the sample is incubated for the desired time period before a detected "value" is presented to the operator.

The occurrence of false positive results may be further reduced by detecting the pyrrole at two or more different wavelengths or voltages. The occurrence of false negatives can be reduced by inclusion of a further reagent which is detectable on correct operation of the method, e.g. a material which undergoes a redox reaction at a different voltage or which releases a fluorescent material on incubation with an aqueous sample.

Figure 2:
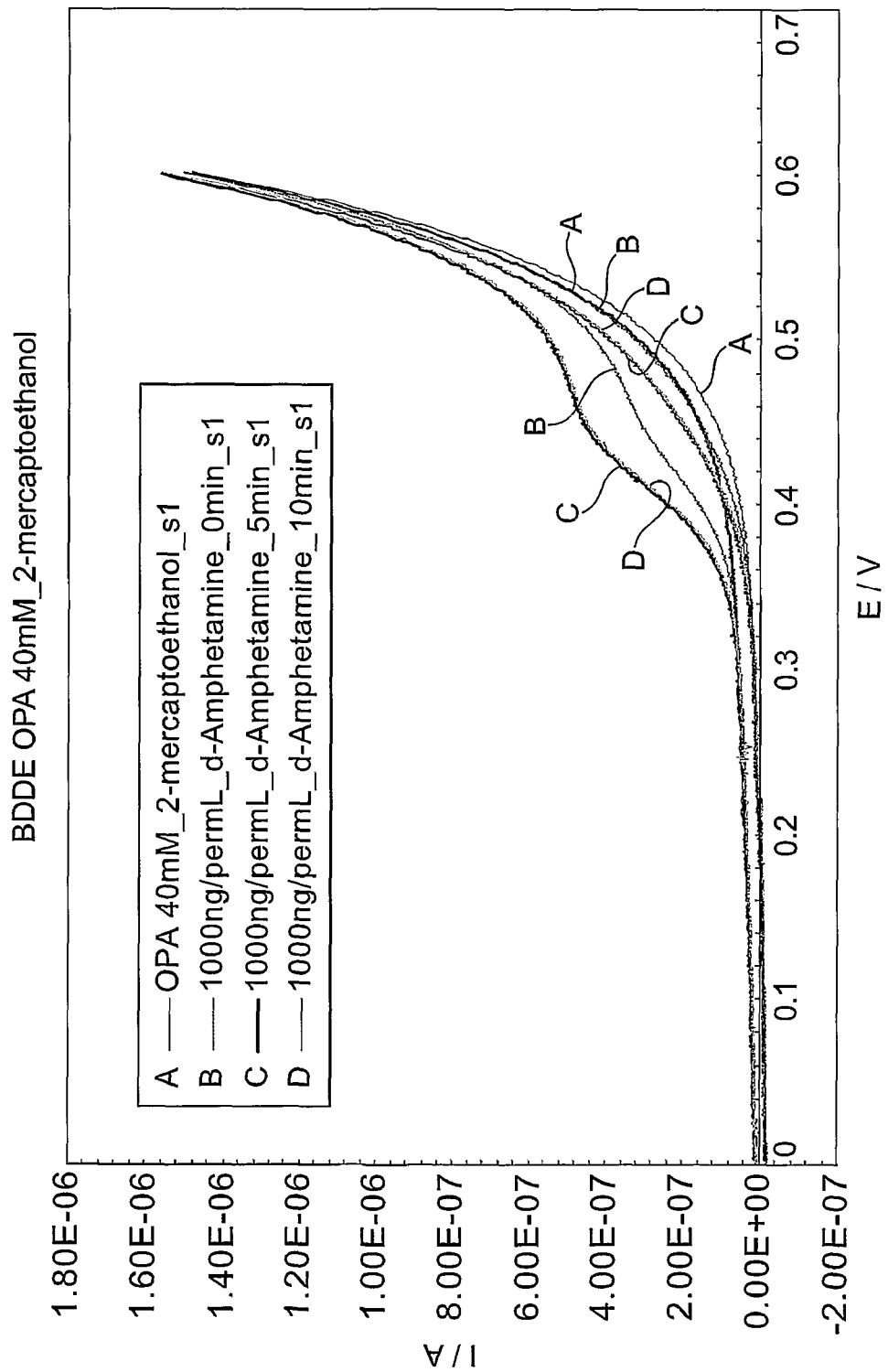
Figure 3:
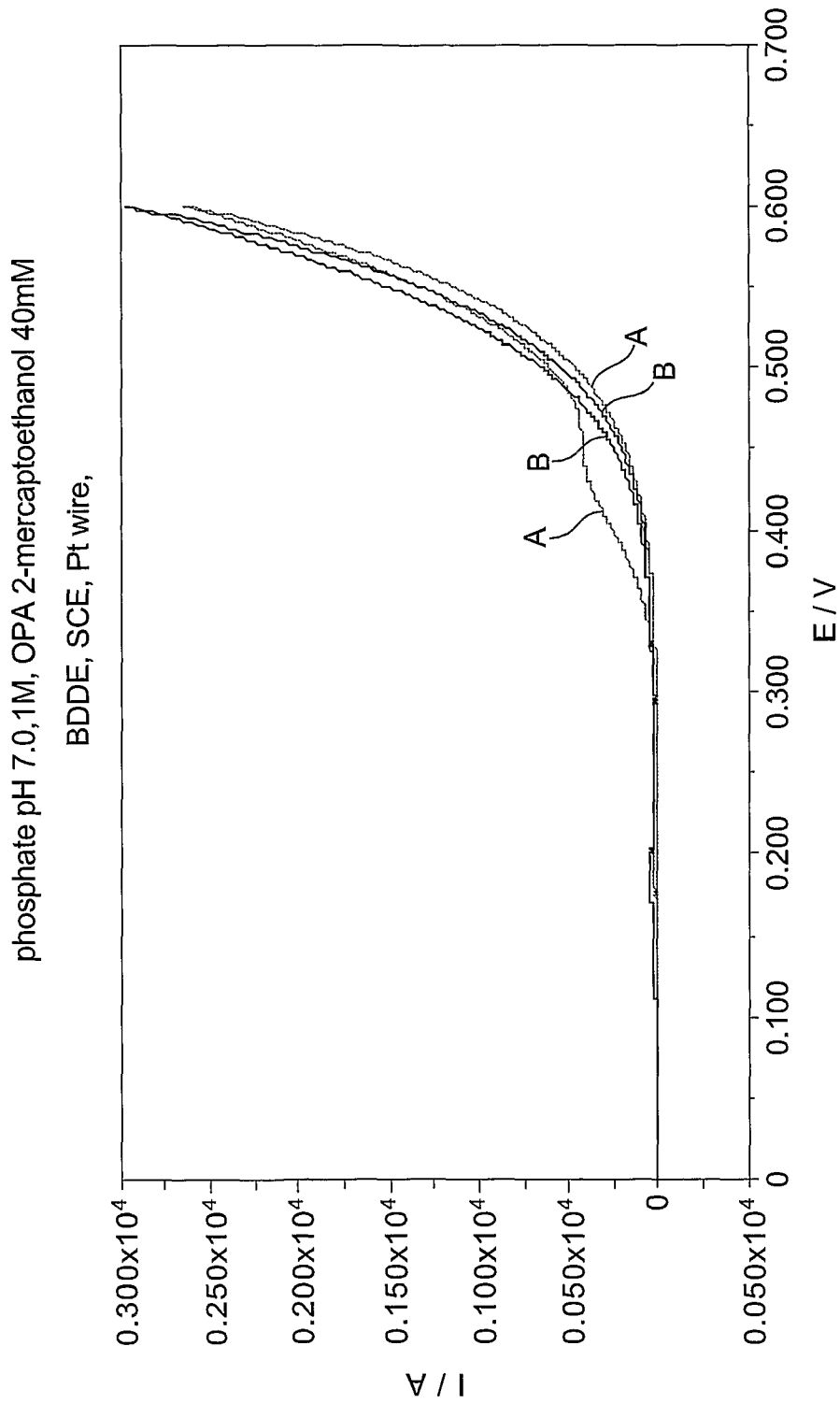

Certain embodiments of the method and cartridges of the invention will now be described in the following non-limiting Examples and with reference to the accompanying drawings, in which:

FIG. 1 is a schematic cross section through a cartridge according to the invention for electrochemical reading; and FIGS. 2 and 3 are voltammograms.

Referring to FIG. 1 there is shown a cartridge 1 having a plastics casing 2 with an aperture 3 for saliva application and containing a cellulosic pad 4 impregnated with a buffer and a thiol. Below pad 4 are disposed three electrodes, a working electrode 5, a counter-electrode 6 and a reference electrode 7. Each electrode is coupled by a wire to a contact plate (8, 9 and 10) on the outside of the case. Working electrode 5 is a carbon electrode coated with an unsaturated cis-dialdehyde. The surface of pad 4 adjacent aperture 3 is covered by a semi-permeable cellulose acetate membrane 11.

In use, the cartridge is removed from its wrapper (not shown), a saliva sample is applied to aperture 3, the cartridge is inserted into a detector causing contact plates 8, 9 and 10 to come into contact with corresponding contacts in the detector and a timer in the detector to start. After the preset incubation time, a voltage is cycled across electrodes 5 and 6, the current values at two preset voltages are determined and compared with calibration data, and a value for the primary amine content of the saliva sample is displayed.

EXAMPLE 1

Detection of Primary Amphetamines 270 mg o-phthalaldehyde were mixed with 5 mL ethanol and approximately 45 mL of aqueous 0.1M phosphate buffer pH 7.0 was added. 200 µL 2-mercapto-ethanol was added and the volume was brought to 50.0 mL to yield the "Reagent Solution".

A sample of the Reagent Solution was placed in a container containing a boron-doped diamond working electrode, a saturated calomel reference electrode and a platinum counter electrode. The voltage across the working and counter-electrodes was cycled between about +1 and about −1 V and the current was recorded. This showed no peaks corresponding to a redox reaction.

Samples of the Reagent Solution containing about 5 mg/mL down to 1 µg/mL of d-amphetamine were then investigated analogously. These all showed a clearly detectable peak, corresponding to a redux reaction of the isoindole, at about +0.47 V. The voltammogram at 1 µg/mL is shown in FIG. 2.

A sample of the Reagent Solution containing 1 µg/mL of (+−)-3,4-methylenedioxy-amphetamine (MDA) also showed a clearly detectable peak at about +0.42 V. This is shown in FIG. 3 (curve A is the response for the MDA-containing sample while curve B is the response for the Reagent Solution itself).

EXAMPLE 2

Absence of Cross-Reactions

Using the technique of Example 1, no cross-reactivity (i.e. detectable redox peak) was shown for the materials set out in Table 1.

TABLE 1

| Compound | Concentration (μg/mL) |
| --- | --- |
| Epicatechin gallate | 100 |
| (+−)-3,4-Methylenedioxymethamphetamine | 10 |
| Epigallocatechin | 100 |
| (+−)-N-Methyl-1-(3,4-methylenedioxyphenyl)-2-butanamine | 10 |
| Fenfluramine | 10 |
| Methamphetamine | 10 |

The invention claimed is:

1. An assay method for the detection of a primary amine analyte in an aqueous body fluid, which method comprises contacting a sample of said body fluid at a pH below 9.5 with a thiol and an unsaturated cis-dialdehyde and testing for the presence of a pyrrole reaction product, wherein the presence of a pyrrole reaction product is tested for electrochemically.

2. The assay method as claimed in claim 1 wherein said cis-dialdehyde is an o-phthalaldehyde.

3. The assay method as claimed in claim 1 or claim 2 wherein said body fluid is urine or saliva.

4. The assay method as claimed in claim 1 or claim 2 wherein said pH below 9.5 is a pH in the range of 6 to 8.

5. The assay method as claimed in claim 1 or claim 2 wherein said body fluid is also subjected to a further assay capable of detecting both primary and secondary amines.

6. The assay method as claimed in claim 1 or claim 2 wherein said primary amine analyte is a primary amphetamine.

7. An assay cartridge comprising a casing having an aperture for placement of a body fluid sample and containing a water-absorbent pad, a thiol, and an unsaturated cis-dialdehyde, and at least two electrodes capable of being in electrical contact through said pad when said pad is moist.

8. The assay cartridge as claimed in claim 7 wherein said thiol and unsaturated cis-dialdehyde are impregated into said pad and said cartridge has a radiation translucent window or aperture allowing radiation from said pad to exit said cartridge.

9. The assay method as claimed in claim 3 wherein said pH below 9.5 is a pH in the range of 6 to 8.

10. The assay method as claimed in claim 3 wherein said body fluid is also subjected to a further assay capable of detecting both primary and secondary amines.

11. The assay method as claimed in claim 4 wherein said body fluid is also subjected to a further assay capable of detecting both primary and secondary amines.

12. The assay method as claimed in claim 3 wherein said primary amine analyte is a primary amphetamine.

13. The assay method as claimed in claim 4 wherein said primary amine analyte is a primary amphetamine.

14. The assay method as claimed in claim 5 wherein said primary amine analyte is a primary amphetamine.

* * * * *